United States Patent [19]

Patel et al.

[11] Patent Number: 5,854,433
[45] Date of Patent: Dec. 29, 1998

[54] VARIABLE ROTATION AND IRRADIATION WEATHERING TESTING MACHINE

[75] Inventors: Bhakti S. Patel, Bensenville; Jacob Tikhtman, Northbrook, both of Ill.

[73] Assignee: Atlas Electric Devices Co., Chicago, Ill.

[21] Appl. No.: 746,378

[22] Filed: Nov. 8, 1996

[51] Int. Cl.⁶ ................................................. G01N 17/00
[52] U.S. Cl. ........................................... 73/865.6; 73/159
[58] Field of Search ................................. 73/865.6, 159; 315/259, 284–286

[56] References Cited

U.S. PATENT DOCUMENTS

| | | |
|---|---|---|
| 4,329,396 | 5/1982 | Kropp . |
| 4,627,287 | 12/1986 | Suga . |
| 4,843,893 | 7/1989 | Huber et al. . |
| 4,874,952 | 10/1989 | Arnaud et al. ........................ 73/865.6 |
| 5,226,318 | 7/1993 | Huber et al. . |
| 5,477,113 | 12/1995 | Christoffersson ....................... 315/284 |
| 5,503,032 | 4/1996 | Tikhtman et al. . |
| 5,552,221 | 9/1996 | So et al. . |

*Primary Examiner*—Robert Raevis
*Attorney, Agent, or Firm*—Gerstman, Ellis & McMillin, Ltd.

[57] ABSTRACT

Material samples may be tested for weathering by a method which comprises securing the samples to a rack which rotates about a central radiation source, and exposing the samples to irradiation from the source at a first intensity of at least about 1.5 SUNS, while rotating the rack at a rate of at least about 6 rpm. Alternatively, a lower radiation intensity may be provided from the same apparatus, using a lower rotation rate. The method may also comprise a step of varying the inductance of a circuit supplying power to the central radiation source as one changes the intensity of the irradiation, to enhance the constancy of spectral distribution of the irradiation at the different intensities.

19 Claims, 1 Drawing Sheet

VARIABLE ROTATION AND IRRADIATION WEATHERING TESTING MACHINE

BACKGROUND OF THE INVENTION

As particularly illustrated in Tikhtman et al. U.S. Pat. No. 5,503,032 and Huber et al. U.S. Pat. Nos. 4,483,893 and 5,226,318, weathering testing machines are provided to test the accelerated ageing characteristics of painted surfaces, fabrics, plastic sheeting and the like. This is accomplished by exposing the materials to be tested in a chamber to high intensity radiation that typically approximates sunlight, under conditions of controlled and sometimes high temperature and/or humidity.

In the machines of the patents cited above, a rotatable rack for carrying the samples to be tested surrounds a xenon lamp, which emits irradiation having a substantial ultraviolet component. The rack is rotated typically at about 1 rpm., to avoid any systematic differences of positioning of the samples in the system. Also, the typical level of irradiation imposed on the samples is about 1 SUN, which is defined in the J-1885 weathering testing standard to be 0.55 watt per square meter at 340 nm. U.V. radiation.

Recently, work is underway relating to further accelerating the ageing of materials by exposing them to an irradiance level that is higher than 1 SUN, for example 2 SUNS (or about 1.1 watts per square meter in accordance with the previous definition). As part of this invention, it has been noted that at such higher light intensities, the irregularity of light irradiance around the rack at the area of the samples becomes bigger, contributing to sample temperature variations. Since the response time of the temperature sensors typically used are generally much lower than 1 minute, weathering testing machines with automated condition control, and which use temperature as a feedback, can show systematic variations in the data as the rack rotates. Also, the samples themselves may be affected in their testing program by these variabilities.

The variations referred to relate to the minor errors which may be created by slight imperfections in the roundness of the rack, a slight eccentricity of the lamp radiation source relative to the rack, slight irregularities of light radiated around the lamp, or the like.

By this invention, the above disadvantages and problems are greatly reduced.

DESCRIPTION OF THE INVENTION

In accordance with this invention, a weathering testing machine comprises a source of radiation which is connected to a power circuit. A power controller is connected to the power circuit, to control the output of the source of radiation. The power controller is capable of causing the source of radiation to emit any of a plurality of different radiation intensities.

An inductive circuit is connected to the power circuit, with the inductive circuit being adjustable to vary the induction of the power circuit depending on the particular radiation intensity being emitted, for the purpose of enhancing the constancy of the spectral distribution of the irradiation at the different radiation intensities.

The weathering testing machine also comprises a rack, which is positioned to be irradiated by the source of irradiation and which is for carrying the samples to be irradiated. Because of the inductive circuit provided by this invention, samples may be irradiated at different radiation intensities as stated above, while the spectral distribution (i.e., percentage of ultraviolet and the various categories of visible and infrared radiation) may be made more constant at the respective different radiation intensities. This provides greater comparability between testing runs, so that results obtained at differing radiation intensities may be more easily compared with each other.

Also by this invention, it is preferred to rotate the rack at a rotation rate of at least 6 rpm, and preferably at least 10 rpm when the intensity of irradiation on the samples is at least 1.5 SUNS. Typically, the desired radiation intensity may be 2 to 4 SUNS while this accelerated rotation rate is provided.

Preferred apparatus of this invention will also be capable of irradiation of samples, when desired, at an intensity of about 1 SUN. If desired in that circumstance, the rotation rate of the rack may be reduced to below 6 rpm, for example down to 1 rpm if desired, in accordance with the prior art. However, substantial advantages are achieved at irradiation intensities of 2, 3, or more SUNS when the rack rotation rate is 6–10 rpm or greater.

Particularly, the response time of temperature sensors which are commonly commercially available is about 6 seconds or so. In that circumstance, it is desirable for the rotation of the rack to take place in about 6 seconds or less (implying 10 rpm or more) since that has the effect of averaging out the various positioning and radiation errors among the various samples at the high radiation intensities of above 1 SUN, where the effects of the systematic errors become more significant unless they are eliminated in accordance with this invention.

The inductive circuit used in this invention may comprise a coil which is connected to a first portion of the inductive circuit, and a movable connector which is connected to a second portion of the inductive circuit. The movable connector electrically connects with the coil at predetermined positions (which are typically spaced from the coil ends) to provide a variable inductance system. The predetermined positions are set to provide the desired constancy of spectral distribution at the particular radiation intensities which may be provided by the particular embodiment of the machine of this invention.

Accordingly, one can test material samples for weathering testing by the process which comprises: securing the samples to a rack which rotates about a central radiation source, and exposing said samples to irradiation from the source at an intensity of at least 1.5 SUNS, while rotating the rack at a rate of at least 6 rpm. One may also vary the inductance of a circuit supplying power to the central radiation source while changing the intensity of the irradiation, to enhance the constancy of spectral distribution of the irradiation at different intensities.

As a result of this, accelerated weathering of samples can take place at the higher radiation intensities, while the process remains highly reproducible, and the spectral distribution of the irradiation remains more constant at differing radiation intensities, so that weathering data of various materials becomes more comparable and thus more useful.

DESCRIPTION OF SPECIFIC EMBODIMENTS

Figure 1:
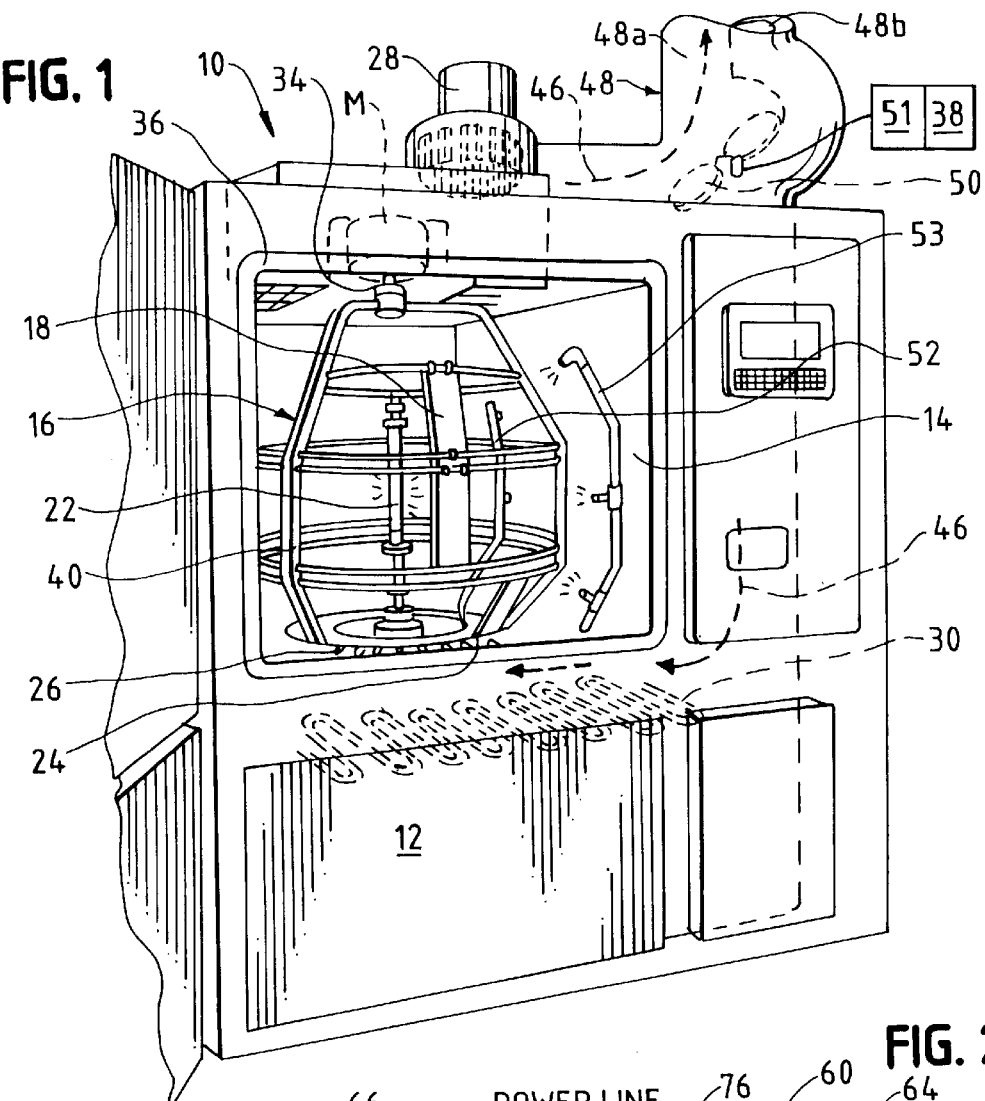
FIG. 1 is a perspective view of a weathering testing machine in accordance with this invention.

Referring to the drawings, a weathering testing device 10 is shown, which comprises a housing 12 defining an upper chamber 14 in which a rack 16 resides, comprising a roughly spherical array of stainless steel struts, to which test samples 18 may be attached in a manner substantially equidistant from a central light source 22, which may be a xenon lamp. This arrangement is similar to that disclosed in U.S. Pat. No. 5,503,032.

At the bottom of upper chamber 14 a circular arrangement of apertures 26 are provided, plus a conical baffle 24, to assist in directing air passing through apertures 26 along test samples 18 carried on the rack.

A conventional resistance-type heater element 30 may be positioned under apertures 26 and the partition that carries them, for helping to control the temperature of the air surrounding the samples. The fitting of xenon lamp 22 may be in accordance with U.S. Pat. No. 5,226,318, including both electrical and water flow conduits for providing the same to xenon lamp 22.

Rack 16 is carried by a first support member or shaft 34 which extends through the top wall 36 of the upper chamber 14. Thus, the connections of various electronic devices carried on rack 16 may pass with shaft 34 through top wall 36 to a microprocessor 38 that is carried in the weathering testing system above top wall 36, in a manner that is safely spaced from both the flowing water and the high electric currents and voltages used with respect to xenon lamp 22.

A motor M is positioned above top wall 36, which rotates shaft 34 and rack 16. Test rack 16 may carry a black panel temperature sensor 40, which is a sensor particularly adapted to sense the temperature directly imparted by the radiation from the xenon lamp. A dry bulb sensor may also be provided at a position more remote from lamp 22 to monitor air temperature. Also, a direct percentage RH humidity sensor may be provided. Each of these can provide signal data to microprocessor 38.

The top wall also defines wall apertures which represent the inlet of a circulatory plenum 46 that circulates air, driven by blower 28, from top to the bottom of chamber 14 and through apertures 26, as propelled by blower 28.

Within plenum 46 is a variably openable cooling air supply vent 48, having a movable damper 50, and comprising air inlet 48b and air outlet 48a. The position of the damper 50 can be controlled by a control member 51 which is, in turn, controlled by the microprocessor 38 in a conventional manner.

Rack water spray or atomizer unit 52 is also provided in upper chamber 14, along with a specimen water sprayer atomizer unit 53, provided for added specific spraying of the specimens when that is desired.

Further details with respect to weathering test machine 10 may be as disclosed in the previously cited U.S. Pat. No. 5,503,032.

Figure 2:
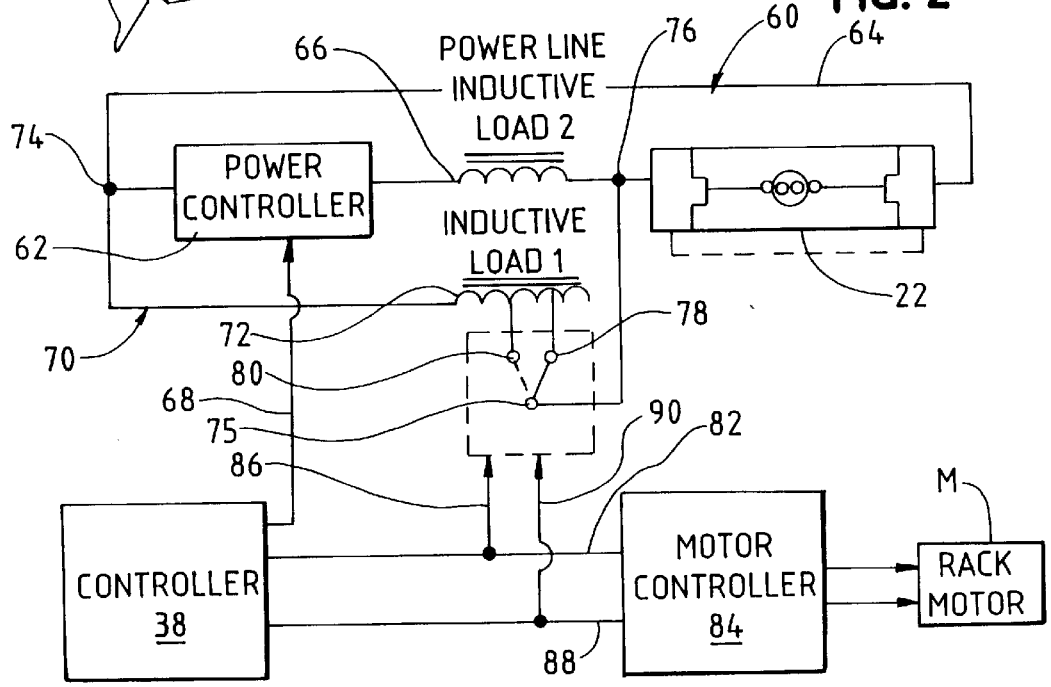
FIG. 2 is a schematic view of the system for controlling the illumination and intensity of the radiation source used in the apparatus of FIG. 1.

Referring to FIG. 2, a power and control system for xenon lamp 22 is disclosed, plus an inductive circuit with variable induction to permit an appropriate change in the induction as the lamp is exposed to differing power levels.

Power circuit 60 comprises a power controller, typically an SCR controller 62, and a conventional loop circuit 64 that connects with both terminals of xenon lamp 22 through a conventional igniter system. Power circuit 60 also comprises an inductive load 66, typically an inductive coil.

The amount of power emitted by power controller 62 may be controlled by microprocessor 38 through line 68, so that the radiation intensity emitted by xenon lamp 22 may comprise at least two levels, for example irradiation level of 1 SUN, as measured at samples 18, or 2 SUNS, measured in the same manner. Alternatively, three or more radiation intensity settings may also be provided including settings of three SUNS or four SUNS, for example.

Inductive circuit 70 comprises a first portion which, in turn, comprises an inductive coil 72 connected by wire to junction 74 of power circuit 60. Inductive circuit 70 also comprises a second portion which, in turn, comprises a switching system 75, which is connected by wire to junction point 76 of the power circuit. Switching system 75 alternatively connects to one of a pair of connector points 78, 80 which, in turn, are connected to differing points along inductive coil 72 at predetermined positions, spaced from each other. Thus, as switch system 75 moves back and forth, the inductance of inductive circuit 70 changes, causing a resulting change in the inductance of power circuit 60. These respective inductances are set by the positioning of connector points 78, 80 to correlate with different power settings for lamp 22 as provided by controller 62, to cause the spectral distribution of the radiation emitted by lamp 22 at the respective, different power settings to be relatively constant.

Thus, when it is desired for the radiation intensity of lamp 22 to equal 1 SUN, for example, a first circuit or a first signal 82 may be activated by controller software 38 to cause motor controller 84 to operate rack motor M so that rack 16 rotates at a desired low rpm, for example 1 rpm. At the same time, a signal 86 causes switch member 75 to connect with switch point 78, which closes the inductive circuit 70 to provide a specific, predetermined induction to power circuit 60 which is compatible with 1 SUN radiation intensity. The signal for that particular radiation intensity is sent via line 68 to power controller 62.

However, when it is desired to operate at 2 SUNS, or some other predetermined, higher level, circuit or signal 88 is activated instead of circuit or signal 82, causing motor controller 84 to operate rack motor M so that rack 16 rotates at 10 rpm, for example. Simultaneously therewith, a signal 90 is sent to switch 75 which causes the switch to flip to connect with switch point 80 rather than point 78. This of course changes the inductive load of circuit 70, having a consequent, desired effect upon power circuit 60, as software 38 signals power controller 62 to operate lamp 22 at a 2 SUNS radiation intensity. Because of the predetermined change in inductance, the spectral distribution of radiation emitted from xenon lamp 22 remains relatively constant, although of doubled intensity relative to the 1 SUN radiation emission.

Thus, the weathering testing machine of this invention can have at least two operating modes of varying radiation intensity, an automatically (if desired) correlated rotation speed of rack 16, and a correlated inductance in the lamp power circuitry, to achieve the advantages discussed above. Alternatively, the rack can rotate at an elevated speed such as 10 rpm for both modes of operation, if that is desired.

The above has been offered for illustrative purposes only, and is not intended to limit the scope of the invention of this application, which are as defined in the claims below.

That which is claimed:

1. A weathering testing machine which comprises:

a source of radiation;

a power controller having a plurality of settings corresponding to predetermined radiation intensity outputs from the source of radiation;

a circuit connected to said source of radiation and said power controller wherein the inductance of said circuit is changed as said power controller settings are changed to cause the spectral distribution of the radiation emitted by said source of radiation to be relatively constant; and a rack positioned to be irradiated by said source of radiation, for carrying samples to be irradiated.

2. The testing machine of claim 1 in which said power controller is an SCR controller.

3. The testing machine of claim 1 in which said source of radiation is a xenon lamp.

4. The testing machine of claim 1 in which said circuit comprises a coil connected to a movable connector to alternatively electrically connect with said coil at predetermined positions spaced from each other.

5. The testing machine of claim 1 in which said rack is rotatable about said source of radiation.

6. The testing machine of claim 5 in which a motor is provided, said motor being capable of rotating said rack about said source of radiation at a rate of at least about 6 rpm.

7. The testing machine of claim 1 in which said source of radiation can selectively irradiate samples on said rack at a first radiation intensity of about 1 SUN or a second radiation intensity of at least about 1.5 SUNS.

8. The testing machine of claim 7 in which a motor is capable of rotating the rack at less than 6 rpm. when the first radiation intensity is being used.

9. A method of weathering testing material samples, which comprises: securing samples to a rack which rotates about a central radiation source, and exposing said samples to irradiation from said source at an intensity of at least about 1.5 SUNS, while rotating said rack at a rate of at least about 6 rpm; rotating samples on said rack at another time while exposing said samples to irradiation from said source at an intensity of about 1 SUN while rotating said rack at a rate of less than 6 rpm; and varying the inductance of a circuit supplying power to the central radiation source while changing the instensity of said irradiation to cause the spectral distribution of said irradiation to be relatively constant at different intensities.

10. A weathering testing machine which comprises:

a source of radiation;

a power controller having a plurality of settings corresponding to predetermined radiation intensity outputs from the source of radiation;

a circuit connected to said source of radiation and said power controller wherein the inductance of said circuit is changed as said power controller settings are changed to cause the spectral distribution of the radiation emitted by said source of radiation to be relatively constant;

a rack, positioned to be irradiated by said source of radiation, for carrying samples to be irradiated;

said rack being rotatable about said source of radiation;

said source of radiation being capable of irradiating samples on said rack at a first radiation intensity of about 1 SUN or a second irradiation intensity of at least about 1.5 SUNS.

11. The testing machine of claim 10 in which a motor is provided, said motor being capable of rotating said rack about said source of radiation at a rate of at least about 6 rpm.

12. The testing machine of claim 11 in which said motor is capable of rotating the rack at less than 6 rpm. when the first radiation intensity is being used.

13. The testing machine of claim 12 in which said inductive circuit comprises a coil, connected to a first portion of said inductive circuit, and a movable connector which is connected to a second portion of said inductive circuit, to alternatively electrically connect with said coil at predetermined positions spaced from each other.

14. The testing machine of claim 13 in which said power controller is an SCR controller.

15. The testing machine of claim 14 in which said source of radiation is a xenon lamp.

16. The method of weathering testing material samples, which comprises: securing said samples to a rack which rotates about a central radiation source; exposing said samples to irradiation from said source at an intensity of at least about 1.5 SUNS while rotating said rack at a rate of at least about 10 rpm., and further comprising the step of varying the inductance of a circuit supplying power to the central radiation source while changing the intensity of said irradiation, to cause the spectral distribution of said irradiation at different intensities to be relatively constant.

17. The method of claim 16 in which said sample is exposed to radiation intensity of about 2 to 4 SUNS.

18. The method of claim 17 in which the changed intensity of said irradiation is changed to about 1 SUN.

19. A method of weathering testing material samples which comprises:

securing said samples to a rack which rotates about a central radiation source;

exposing said samples to irradiation at a first intensity;

changing the intensity of irradiation from said central radiation source to a second intensity; and simultaneously changing the inductance of the circuit powering said central radiation source to cause the spectral distribution of said irradiation at said first and second intensities to be relatively constant.

* * * * *